US008518961B2

(12) United States Patent
Ottinger

(10) Patent No.: US 8,518,961 B2
(45) Date of Patent: Aug. 27, 2013

(54) PHARMACEUTICAL COMPOSITIONS COMPRISING A CAMPTOTHECIN DERIVATE

(75) Inventor: Isabel Ottinger, Freiburg (DE)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 1270 days.

(21) Appl. No.: 11/718,275

(22) PCT Filed: Nov. 17, 2005

(86) PCT No.: PCT/EP2005/012334
§ 371 (c)(1),
(2), (4) Date: Apr. 30, 2007

(87) PCT Pub. No.: WO2006/053755
PCT Pub. Date: May 26, 2006

(65) Prior Publication Data
US 2008/0125450 A1     May 29, 2008

Related U.S. Application Data

(60) Provisional application No. 60/629,757, filed on Nov. 19, 2004.

(51) Int. Cl.
*A61K 31/47*     (2006.01)

(52) U.S. Cl.
USPC ........................................................ 514/280

(58) Field of Classification Search
None
See application file for complete search history.

(56) References Cited

U.S. PATENT DOCUMENTS

| 5,597,829 | A | 1/1997 | Hausheer et al. |
| 5,880,133 | A | 3/1999 | Hausheer et al. |
| 6,242,457 | B1 | 6/2001 | Penco et al. |
| 6,653,319 | B1 | 11/2003 | Xiang et al. |
| 2002/0150615 | A1 | 10/2002 | Sands et al. |
| 2004/0009229 | A1 | 1/2004 | Unger et al. |
| 2004/0171560 | A1 | 9/2004 | Mukherjee et al. |
| 2005/0142225 | A1 | 6/2005 | Kysilka et al. |
| 2005/0191343 | A1 * | 9/2005 | Liang |
| 2006/0269613 | A1 | 11/2006 | Ogawa et al. |

FOREIGN PATENT DOCUMENTS

| EP | 0539319 | 4/1993 |
| EP | 0645145 | 3/1995 |
| EP | 1 426 044 A | 6/2004 |
| JP | 2003/267891 | 9/2003 |
| JP | 2004/043355 | 2/2004 |
| RU | 2143919 | 1/2000 |
| WO | WO 94/14415 | 7/1994 |
| WO | WO 96/39143 | 12/1996 |
| WO | WO98/30205 | 7/1998 |
| WO | WO99/06024 | 2/1999 |
| WO | WO 99/06031 | 2/1999 |
| WO | 99/56727 | 11/1999 |
| WO | 00/48571 A1 | 8/2000 |
| WO | WO00/71163 | 11/2000 |
| WO | WO 00/71163 A1 * | 11/2000 |
| WO | WO 01/10443 | 2/2001 |
| WO | WO 01/30351 | 5/2001 |
| WO | WO 03/032906 | 4/2003 |
| WO | WO 03/057128 | 7/2003 |
| WO | WO 03/103596 | 12/2003 |
| WO | WO 03/103714 | 12/2003 |
| WO | WO 2004/002454 | 1/2004 |
| WO | WO 2005/042539 | 5/2005 |
| WO | WO 2005/060871 | 7/2005 |
| WO | 2006/053755 | 5/2006 |

OTHER PUBLICATIONS

Pratesi et al., Anti-Cancer Drugs, Jul. 2004, vol. 15(6), pp. 545-552; Abstract only.*
Lieberman, Pharmaceutical Dosage Forms: vol. 2: Disperse Systems, 1996, Marcel Dekker, Inc., pp. 63-67.*
Journal of Liposome Research, vol. 14, Nos. 1-2, pp. 87-109 (2004) and Database Biosis "Online" Biosciences Information Service, Stano Pasquale et al.: "Novel Camptothecin analogue (Gimatecan)-containing liposomes prepared by the ethanol injection method" (2004), Database accession No. PREV200400465331.
Cortesi et al., "Formulation study for the antitumor drug camptothecin: liposomes, micellar solutions and a microemulsion," International Journal of Pharmaceutics, vol. 159, pp. 95-103 (1997).
Strickley, R., "Solubilizing Excipients in Oral and Injectable Formulations" Pharmaceutical Research, vol. 21, No. 2, Feb. 2004, pp. 201-230.
Hua et al., "Preparation and evaluation of microemulsion of vinpocetine for transdermal delivery" Pharmazie, 59: 274-278 (2004).
English Translation of an Office Action for corresponding Japanese Patent Application No. JP2007541793, issued Nov. 15, 2011.

* cited by examiner

*Primary Examiner* — Savitha Rao
*Assistant Examiner* — Gregg Polansky
(74) *Attorney, Agent, or Firm* — Lucas & Mercanti, LLP

(57) ABSTRACT

The present invention relates to novel pharmaceutical compositions in which the active agent is a topoisomerase I inhibitor, in particular a camptothecin derivative, that is useful for the treatment and prevention of proliferative diseases including cancer.

12 Claims, No Drawings ns961 B2

PHARMACEUTICAL COMPOSITIONS COMPRISING A CAMPTOTHECIN DERIVATE

This application claims benefit of U.S. Provisional Application No. 60/629,757, filed Nov. 19, 2004.

The present invention relates to novel pharmaceutical compositions in which the active agent is a topoisomerase I inhibitor, in particular a camptothecin derivative, that is useful for the treatment and prevention of proliferative diseases including cancer.

BACKGROUND OF THE INVENTION

Camptothecin derivatives are a class of compounds described in U.S. Pat. No. 6,242,457, the contents of which are incorporated herein by reference. Camptothecin derivatives, such as those disclosed in U.S. Pat. No. 6,242,457, present highly specific difficulties in relation to administration generally and galenic compositions in particular, including in particular problems of drug bioavailability because these derivatives have very poor solubility.

SUMMARY OF THE INVENTION

In accordance with the present invention it has now surprisingly been found that stable pharmaceutical compositions with camptothecin derivatives, including but not limited to 7-t-butoxyiminomethylcamptothecin, have particularly interesting bioavailability characteristics. These novel compositions have been found to meet or substantially reduce the difficulties encountered previously. It has been shown that the compositions of the invention may enable effective dosaging with concomitant enhancement of bioavailability as well as reduced variability of absorption/bioavailability levels for and between individual patients. Thus, the invention may achieve effective therapy with tolerable dosage levels of such camptothecin derivatives, and may permit closer standardization and optimization of daily dosage requirements for each individual. Consequently, occurrence of potential undesirable side-effects is diminished and overall cost of therapy may be reduced.

DETAILED DESCRIPTION OF THE INVENTION

In a first aspect the present invention provides a spontaneously dispersible pharmaceutical composition comprising a camptothecin derivative.

The spontaneously dispersible pharmaceutical composition is hereinafter also referred to as a "composition of the invention". It is preferably a microemulsion preconcentrate.

Terms used in the specification have the following meanings:

"Active agent" as used herein means a camptothecin derivative, such as those disclosed in U.S. Pat. No. 6,242,457.

"Poorly water soluble" as used herein means having a solubility in water at 20° C. of less than 1%, for example 0.01% weight/volume, i.e. a "sparingly soluble to very slightly soluble drug" as described in Remington: The Science and Practice of Pharmacy, 19$^{th}$ Edition, Ed. A. R. Gennaro, Mack Publishing Company, US, 1995, vol. 1, p 195.

"Bioavailable" as used herein with reference to a composition means the composition provides a maximum concentration of the active agent in that composition in a use environment that is at least 1.5 fold that of a control comprising an equivalent quantity of the undispersed drug.

"Spontaneously dispersible pharmaceutical composition" as used herein means a composition that contains an active agent herein defined and is capable of producing colloidal structures—when diluted with an aqueous medium, for example water, or in gastric juices. The colloidal structures are preferably liquid droplets in the microemulsion size range. Solid drug particles, either crystalline or amorphous, of mean diameter greater than 200 nm may also be present. The spontaneously dispersible pharmaceutical composition is preferably a microemulsion preconcentrate.

"Microemulsion preconcentrate" as used herein means a composition which spontaneously forms a microemulsion in an aqueous medium, for example, in water, for example on dilution of 1:1 to 1:300, preferably 1:1 to 1:70, but especially 1:1 to 1:10 or in the gastric juices after oral application.

"Microemulsion" as used herein means a translucent, slightly opaque, opalescent, non-opaque or substantially non-opaque colloidal dispersion that is formed spontaneously or substantially spontaneously when its components are brought into contact with an aqueous medium. A microemulsion is thermodynamically stable and typically contains dispersed droplets of a mean diameter less than about 200 nm (2000 Å). Generally microemulsions comprise droplets or liquid nanoparticles that have a mean diameter of less than about 150 nm (1500 Å); typically less than 100 nm, generally greater than 10 nm, and they are stable over periods up to 24 hours or longer.

Microemulsions offer greater ease of preparation due to spontaneous formation, thermodynamic stability, transparent and elegant appearance, increased drug loading, enhanced penetration through the biological membranes, increased bioavailability, and less inter- and intra-individual variability in drug pharmacokinetics than coarse emulsions. Further characteristics of microemulsions can be found in United Kingdom patent specification GB 2,222,770; Rosof, *Progress in Surface and Membrane Science*, 12, 405 et seq. Academic Press (1975); Friberg, *Dispersion Science and Technology*, 6 (3), 317 et seq. (1985); and Muller et al. *Pharm. Ind.*, 50 (3), 370 et seq. (1988)].

In another aspect, the present invention provides a spontaneously dispersible pharmaceutical composition comprising a camptothecin derivative, and a carrier medium comprising a lipophilic component, a surfactant, a hydrophilic component and optionally a co-solvent.

Preferably the spontaneously dispersible pharmaceutical composition is suitable for oral administration.

The camptothecin derivatives, have poor water solubility characteristics and display a water solubility of below 0.001%, e.g. 0.001 to 0.0001%.

The active agent is preferably used in free base form.

In another aspect, the present invention provides a microemulsion preconcentrate comprising a camptothecin derivative. Especially interesting is that the drug load achieved within the microemulsion pre-concentrates is significantly higher than within the single excipients indicating an over-additive solubility of the camptothecin derivatives within the microemulsion preconcentrates.

In a fourth aspect, the present invention provides a microemulsion preconcentrate comprising a camptothecin derivative and a carrier medium that comprises a lipophilic component, a surfactant, a hydrophilic component and a optionally co-solvent.

The microemulsion preconcentrate preferably forms an o/w (oil-in-water) microemulsion when diluted with water.

Preferably the relative proportions of the lipophilic component(s), the surfactant(s), the hydrophilic component(s), and optionally the co-solvent(s) lie within the "Microemulsion" region on a standard three way plot graph. These phase diagrams, can be generated in a conventional manner as described in e.g. GB 2,222,770 or WO 96/13273.

In another aspect, the present invention provides a microemulsion comprising a camptothecin derivative.

The microemulsion is preferably an o/w (oil-in-water) microemulsion.

In another aspect, the present invention provides a microemulsion comprising a camptothecin derivatives, a lipophilic component, a surfactant, water, a hydrophilic component and optionally a co-solvent The colloidal structures of the microemulsion form spontaneously or substantially spontaneously when the components of the composition of the invention are brought into contact with an aqueous medium, e.g. by simple shaking by hand for a short period of time, for example for 10 seconds. The compositions of the invention are thermodynamically stable, e.g. for at least 15 minutes or up to 4 hours, even to 24 hours or longer. Typically, they contain dispersed structures, i.e. droplets or liquid nanoparticles of a mean diameter less than about 200 nm (2,000 Å), e.g. less than about 150 nm (1,500 Å), typically less than 100 nm (1,000 Å), generally greater than 10 nm (100 Å) as measured by standard light scattering techniques, e.g. using a MALVERN ZETASIZER 3000™ particle characterising machine. Solid drug particles of mean diameter greater than 200 nm may also be present. The proportion of particles present may be temperature dependent.

The active agent is an inhibitor of topoisomerase I (Topo I inhibitor) and is therefore capable of preventing disease symptoms that are caused inter alia by the activation of the topoisomerase I receptor.

More specifically the active agent is a camptothecin derivative. This class of compounds is described in U.S. Pat. No. 6,242,457.

Preferred active agents, which are described in U.S. Pat. No. 6,242,457, include:
7-methoxyiminomethylcamptothecin;
7-methoxyiminomethyl-10-hydroxycamptothecin;
7-(ter-butoxycarbonyl-2-propoxy)iminomethylcamptothecin;
7-ethoxyiminomethylcamptothecin;
7-isopropoxyiminomethylcamptothecin;
7-(2-methylbutoxy)iminomethylcamptothecin;
7-t-butoxyiminomethylcamptothecin;
7-t-butoxyiminomethyl-10-hydroxycamptothecin;
7-t-butoxyiminomethyl-10-methoxycamptothecin;
7-(4-hydroxybutoxy)iminomethylcamptothecin;
7-triphenylmethoxyiminomethylcamptothecin;
7-carboxymethoxyiminomethylcamptothecin;
7-(2-amino)ethoxyiminomethylcamptothecin;
7-(2-N,N-dimethylamino)ethoxyiminomethylcamptothecin;
7-allyloxyiminomethylcamptothecin;
7-cyclohexyloxyiminoethylcamptothecin;
7-cyclohexylmethoxyiminomethylcamptothecin;
7-cyclooctyloxyiminomethylcamptothecin;
7-cyclooctylmethoxyiminomethylcamptothecin;
7-benzyloxyiminomethylcamptothecin;
7-[(1-benzyloxyimino)-2-phenylethyl]camptothecin;
7-(1-benzyloxyimino)ethylcamptothecin;
7-phenoxyiminomethylcamptothecin;
7-(1-t-butoxyimino)ethylcamptothecin;
7-p-nitrobenzyloxyiminomethylcamptothecin;
7-p-methylbenzyloxyiminomethylcamptothecin;
7-pentafluorobenzyloxyiminomethylcamptothecin;
7-p-phenylbenzyloxyiminomethylcamptothecin;
7-[2-(2,4-difluorophenyl)ethoxy]iminomethylcamptothecin;
7-(4-t-butylbenzyloxy)iminomethylcamptothecin;
7-(1-adamantyloxy)iminomethylcamptothecin;
7-(1-adamantylmethoxy)iminomethylcamptothecin;
7-(2-naphthyloxy)iminomethylcamptothecin;
7-(9-anthrylmethoxy)iminomethylcamptothecin;
7-oxiranylmethoxyiminomethylcamptothecin;
7-(6-uracyl)methoxyiminomethylcamptothecin;
7-[2-(1-uracyl)ethoxy]iminomethylcamptothecin;
7-(4-pyridyl)methoxyiminomethylcamptothecin;
7-(2-thienyl)methoxyiminomethylcamptothecin;
7-[(N-methyl)-4-piperidinyl]methoxyiminomethylcamptothecin;
7-[2-(4-morpholininyl)ethoxy]iminomethylcamptothecin;
7-(benzoyloxyiminomethyl)camptothecin;
7-[(1-hydroxyimino)-2-phenylethyl]camptothecin;
7-ter-butyloxyiminomethylcamptothecin-N-oxide; and
7-methoxyiminomethylcamptothecin N-oxide.

In a very preferred embodiment of the invention, the topoisomerase I inhibitor of formula I has the following structure known as Compound A:

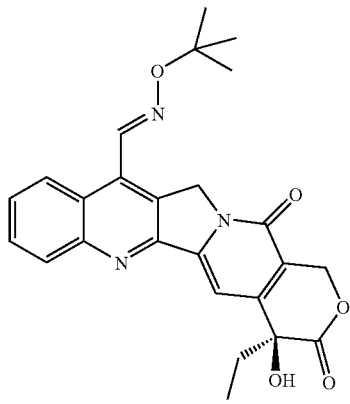

Compound A

The preferred and especially preferred active agents, in free or pharmaceutically acceptable salt form, may be prepared as described in U.S. Pat. No. 6,424,457. As mentioned therein, they may be in the form of their possible enantiomers, diastereoisomers and relative mixtures, the pharmaceutically acceptable salts thereof and their active metabolites.

In accordance with the present invention the active agent may be present in an amount by weight of up to about 20% by weight of the composition of the invention, e.g. from about 0.05% by weight. The active agent is preferably present in an amount of 0.5 to 15% by weight of the composition.

The active agent is poorly water soluble so it is carried in a carrier medium.

In some embodiments of the compositions of the invention the carrier medium comprises a lipophilic component, a surfactant, and a hydrophilic component. In other embodiments the carrier medium comprises a lipophilic component, a surfactant, a hydrophilic component and a co-solvent.

The lipophilic component comprises one or more lipophilic substances. The hydrophilic component comprises one or more hydrophilic substances. The carrier medium can contain one or more surfactants. The carrier medium can contain one or more co-solvents.

The compositions of the invention can include a variety of additives including antioxidants, antimicrobial agents, enzyme inhibitors, stabilizers, preservatives, flavours, sweeteners and further components such as those described in Fiedler, H. P. "Lexikon der Hilfsstoffe für Pharmazie, Kosmetik und angrenzende Gebiete", Editio Cantor, D-7960 Aulendorf, 4th revised and expanded edition (1996). These additives will conveniently be dissolved in the carrier medium.

The compositions of the invention include a lipophilic component or phase. The active agent may be contained in this component of the carrier medium. The lipophilic component (when present) is preferably characterized by a low HLB value of less than 10, e.g. up to 8.

Suitable lipophilic components include:

1) Glyceryl Mono-$C_6$-$C_{14}$-Fatty Acid Esters

These are obtained esterifying glycerol with vegetable oil followed by molecular distillation. Monoglycerides suitable for use in the compositions of the invention include both symmetric (i.e. β-monoglycerides) as well as asymmetric monoglycerides α-monoglycerides. They also include both uniform glycerides (in which the fatty acid constituent is composed primarily of a single fatty acid) as well as mixed glycerides (i.e. in which the fatty acid constituent is composed of various fatty acids) The fatty acid constituent may include both saturated and unsaturated fatty acids having a chain length of from e.g. $C_8$-$C_{14}$. Particularly suitable are caprylic or lauric acid monoglycerides which are commercially available, e.g. under the trade names Imwitor® 308 or Imwitor® 312, respectively, from e.g. sasol. For example Imwitor® 308 comprises at least 80% monoglycerides and exhibits the following additional characterising data: free glycerol max 6%, acid value max. 3, saponification value 245-265, iodine value max. 1, water content max. 1%. Typically it comprises 1% free glycerol, 90% monoglycerides, 7% diglycerides, 1% triglycerides (H. Fiedler, loc. cit., volume 1, page 798). A further example is Capmul MCM C8 from Abitec Corporation.

2) Mixtures of Mono- and Di-Glycerides of $C_6$-$C_{18}$ Fatty Acids

These include both symmetric (i.e. β-monoglycerides and α,α¹-diglycerides) as well as asymmetric mono- and di-glycerides (i.e. α-monoglycerides and α,β-diglycerides) and acetylated derivatives thereof. They also include both uniform glycerides (in which the fatty acid constituent is composed primarily of a single fatty acid) as well as mixed glycerides (i.e. in which the fatty acid constituent is composed of various fatty acids) and any derivatives thereof with lactic or citric acid. The fatty acid constituent may include both saturated and unsaturated fatty acids having a chain length of from e.g. $C_8$-$C_{10}$. Particularly suitable are mixed caprylic and capric acid mono- and di-glycerides as commercially available, e.g. under the trade name Imwitor® 742 or Imwitor 928, from e.g. sasol. For example Imwitor® 742 comprises at least 45% monoglycerides and exhibits the following additional characterising data: free glycerol max. 2%, acid value max. 2, saponification value 250-280, iodine value max. 1, water max. 2% (H. Fiedler, loc. cit., vol 1, page 798). Other suitable mixtures comprise mono/diglycerides of caprylic/capric acid in glycerol as known and commercially available under e.g. the trade name Capmul® MCM from e.g. Abitec Corporation. Capmul® MCM exhibits the following additional characterising data: acid value 2.5 max., alpha-Mono (as oleate) 80% min., free glycerol 2.5% max., iodine value 1 max., chain length distribution: caproic acid (C6) 3% max., caprylic acid (C8) 75% min., capric acid (C10) 10% min., lauric acid (C12) 1.5% max., moisture (by Karl Fisher) 0.5% max. (manufacturer information). Suitable examples of mono-/digicyerides with additional derivatization with lactic or citric acid are those marketed under the brand names of Imwitor 375, 377 or 380 by sasol. Furthermore, the fatty acid constituent may include both saturated and unsaturated fatty acids having a chain length of from e.g. $C_{16}$-$C_{18}$. A suitable example is Tegin® O (glyceryl oleate) exhibiting the following additional characterising data: monoglyceride content 55-65%, peroxide value max. 10, water content max. 1%, acid value max. 2, iodine value 70-76, saponification value 158-175, free glycerol max. 2%, (manufacturer information).

3) Glyceryl Di-$C_6$-$C_{18}$-Fatty Acid Esters

These include symmetric (i.e. α,α¹-diglycerides) and asymmetric diglycerides (i.e. α,β-diglycerides) and acetylated derivatives thereof. They also include both uniform glycerides (in which the fatty acid constituent is composed primarily of a single fatty acid) as well as mixed glycerides (i.e. in which the fatty acid constituent is composed of various fatty acids) and any acetylated derivatives thereof. The fatty acid constituent can include both saturated and unsaturated fatty acids having a chain length of from $C_6$-$C_{18}$, e.g. $C_6$-$C_{16}$, e.g. $C_8$-$C_{10}$, e.g. $C_8$. Particularly suitable is caprylic diglycerides, which is commercially available, e.g. under the trade name Sunfat® GDC-S, e.g. from Taiyo Kagaku Co., Ltd. Sunfat® GDC-S has an acid value of about 0.3, a diglyceride content of about 78.8%, and a monoester content of about 8.9.

4) Medium Chain Fatty Acid Triglyceride

These include triglycerides of saturated fatty acid having 6 to 12, e.g. 8 to 10, carbon atoms. Suitable medium chain fatty acid triglycerides are those known and commercially available under the trade names Acomed®, Myritol®, Captex®, Neobee®M 5 F, Miglyol®810, Miglyol®812, Miglyol®818, Mazol®, Sefsol®860, Sefsol®870; Miglyol®812 being the most preferred. Miglyol®812 is a fractionated coconut oil comprising caprylic-capric acid triglycerides and having a molecular weight of about 520 Daltons. Fatty acid composition =$C_6$ max. about 3%, $C_8$ about 50 to 65%, $C_{10}$ about 30 to 45%, $C_{12}$ max 5%; acid value about 0.1; saponification value about 330 to 345; iodine value max 1. Miglyol® 812 is available from Condea. Neobee® M 5 F is a fractionated caprylic-capric acid triglyceride available from coconut oil; acid value max. 0.2; saponification value about 335 to 360; iodine value max 0.5, water content max. 0.15%, $D.^{20}$ 0.930-0.960, $n_D^{20}$ 1.448-1.451 (manufacturer information). Neobee® M 5 F is available from Stepan Europe. A further example is Miglyol 829 containing additionally esters with succinic acid.

5) Glyceryl Mono-$C_{16}$-$C_{18}$-Fatty Acid Esters

These are obtained esterifying glycerol with vegetable oil followed by molecular distillation. Monoglycerides suitable for use in the compositions of the invention include both symmetric (i.e. β-monoglycerides) as well as asymmetric monoglycerides α-monoglycerides. They also include both uniform glycerides (in which the fatty acid constituent is composed primarily of a single fatty acid) as well as mixed glycerides (i.e. in which the fatty acid constituent is composed of various fatty acids) The fatty acid constituent may include both saturated and unsaturated fatty acids having a chain length of from e.g. $C_{16}$-$C_{18}$. Suitable examples include GMOrphic by Eastman, Rylo MG20 distilled monoglyceride by Danisco Ingredients, or Monomuls 90-O18 by Henkel.

For example GMOrphic®-80 (glyceryl monooleate) exhibits the following additional characterising data: monoglyceride content min. 94%, C18:1 content 75% min., peroxide value max. 2.5, C18:2+C18:3 max. 15%, C16:0+C18:0+C20:0 max. 10%, water max. 2%, acid value max. 3, iodine value 65-75, saponification value 155-165, free glycerine max. 1%, hydroxyl number 300-330 (manufacturer information).

6) Mixed Mono-, Di-, Tri-Glycerides

These include mixed mono-, di-, tri-glycerides that are commercially available under the trade name Maisine® from Gattefossé. They are transesterification products of corn oil and glycerol. Such products are comprised predominantly of linoleic and oleic acid mono-, di- and tri-glycerides together with minor amounts of palmitic and stearic acid mono-, di- and tri-glycerides (corn oil itself being comprised of ca. 56% by weight linoleic acid, 30% oleic acid, ca. 10% palmitic and ca. 3% stearic acid constituents). Physical characteristics are: free glycerol max 10%, monoglycerides ca. 40%, diglycerides ca. 40%, triglycerides ca. 10%, free oleic acid content ca. 1%. Further physical characteristics are: acid value max. 2, iodine value of 85-105, saponification value of 150-175, mineral acid content=0. The fatty acid content for Maisine® is typically: palmitic acid ca. 11%, stearic acid ca. 2.5%, oleic acid ca. 29%, linoleic acid ca. 56%, others ca. 1.5% (H. Fiedler, loc. cit., volume 2, page 958; manufacturer information).

Mixed mono-, di-, tri-glycerides preferably comprise mixtures of $C_8$ to $C_{10}$ or $C_{12-20}$ fatty acid mono-, di- and tri-glycerides, especially mixed $C_{16-18}$ fatty acid mono-, di- and triglycerides. The fatty acid component of the mixed mono-, di- and tri-glycerides may comprise both saturated and unsaturated fatty acid residues. Preferably however they are predominantly comprised of unsaturated fatty acid residues; in particular $C_{18}$ unsaturated fatty acid residues. Suitably the mixed mono-, di-, tri-glycerides comprise at least 60%, preferably at least 75%, more preferably at least 85% by weight of a $C_{18}$ unsaturated fatty acid (for example linolenic, linoleic and oleic acid) mono-, di- and tri-glycerides. Suitably the mixed mono-, di-, tri-glycerides comprise less than 20%, for example about 15% or 10% by weight or less, saturated fatty acid (for example palmitic and stearic acid) mono-, di- and tri-glycerides. Mixed mono-, di-, tri-glycerides are preferably predominantly comprised of mono- and di-glycerides; for example mono- and di-glycerides comprise at least 50%, more preferably at least 70% based on the total weight of the lipophilic phase or component. More preferably, the mono- and di-glycerides comprise at least 75% (for example about 80% or 85% by weight of the lipophilic component. Preferably monoglycerides comprise from about 25 to about 50%, based on the total weight of the lipophilic component, of the mixed mono-, di-, tri-glycerides. More preferably from about 30 to about 40% (for example 35 to 40%) monoglycerides are present. Preferably diglycerides comprise from about 30 to about 60%, based on the total weight of the lipophilic component, of the mixed mono-, di-, tri-glycerides. More preferably from about 40 to about 55% (for example 48 to 50%) diglycerides are present. Triglycerides suitably comprise at least 5% but less than about 25%, based on the total weight of the lipophilic component, of the mixed mono-, di-, tri-glycerides. More preferably from about 7.5 to about 15% (for example from about 9 to 12%) triglycerides are present. Mixed mono-, di-, tri-glycerides may be prepared by admixture of individual mono-, di- or tri-glycerides in appropriate relative proportion. Conveniently however they comprise trans-esterification products of vegetable oils, for example almond oil, ground nut oil, olive oil, peach oil, palm oil or, preferably, corn oil, sunflower oil or safflower oil and most preferably corn oil, with glycerol. Such transesterification products are generally obtained as described in GB 2 257 359 or WO 94/09211. Preferably some of the glycerol is first removed to give a "substantially glycerol free batch" when soft gelatine capsules are to be made. Purified transesterification products of corn oil and glycerol provide particularly suitable mixed mono-, di-, and tri-glycerides hereinafter referred to as "refined oil" and produced according to procedures described in United Kingdom patent specification GB 2,257,359 or international patent publication WO 94/09211.

7) Acetylated Monoglycerides (C18)

These include Myvacet 9-45.

8) Propylene Glycol Monofatty Acid Esters

The fatty acid constituent may include both saturated and unsaturated fatty acids having a chain length of from e.g. $C_8$-$C_{12}$. Particularly suitable are propylene glycol mono ester of caprylic and lauric acid as commercially available, e.g. under the trade names Sefsol® 218, Capryol®90 or Lauroglycol®90, from e.g. Nikko Chemicals Co., Ltd. or Gattefossé or Capmul PG-8 from Abitec Corporation. For example Lauroglycol®90 exhibits the following additional characterising data: acid value max. 8, saponification value 200-220, iodine value max. 5, free propylene glycol content max. 5%, monoester content min. 90%; Sefsol® 218 exhibits the following additional characterising data: acid value max. 5, hydroxy value 220-280 (H. Fiedler, loc. cit., vol 2, page 906, manufacturer information).

9) Propylene Glycol Mono- and Di-Fatty Acid Esters

These include Laroglycol FCC and Capryol PGMC.

10) Propylene Glycol Diesters

Propylene glycol di-fatty acid esters such as propylene glycol dicaprylate (which is commercially available under the trade name Miglyol® 840 from e.g. sasol; H. Fiedler, loc. cit., volume 2, page 1008) or Captex 200 from Abitec Corporation.

11) Propylene Glycol Monoacetate and Propylene Glycol Diacetate

12) Transesterified Ethoxylated Vegetable Oils

These include transesterified ethoxylated vegetable oils such as those obtained by reacting various natural vegetable oils (for example, corn oil, maize oil, castor oil, kernel oil, almond oil, ground nut oil, olive oil, soybean oil, sunflower oil, safflower oil and palm oil, or mixtures thereof) with polyethylene glycols that have an average molecular weight of from 200 to 800, in the presence of an appropriate catalyst. These procedures are described in United States patent specification U.S. Pat. No. 3,288,824. Transesterified ethoxylated corn oil is particularly preferred.

Transesterified ethoxylated vegetable oils are known and are commercially available under the trade name Labrafil® (H. Fiedler, loc. cit., vol 2, page 880). Examples are Labrafil® M 2125 CS (obtained from corn oil and having an acid value of less than about 2, a saponification value of 155 to 175, an HLB value of 3 to 4, and an iodine value of 90 to 110), and Labrafil® M 1944 CS (obtained from kernel oil and having an acid value of about 2, a saponification value of 145 to 175 and an iodine value of 60 to 90). Labrafil® M 2130 CS (which is a transesterification product of a $C_{12-18}$ glyceride and polyethylene glycol and which has a melting point of about 35 to 40° C., an acid value of less than about 2, a saponification value of 185 to 200 and an iodine value of less than about 3) may also be used. The preferred transesterified ethoxylated vegetable oil is Labrafil® M 2125 CS which can be obtained, for example, from Gattefossé, Saint-Priest Cedex, France.

13) Sorbitan Fatty Acid Esters

Such esters include e.g. sorbitan mono $C_{12-18}$ fatty acid esters, or sorbitan tri $C_{12-18}$ fatty acid esters are commercially available under the trade mark Span® from e.g. uniqema. An especially preferred product of this class is e.g. Span® 20 (sorbitan monolaurate) or Span® 80 (sorbitan monooleate) (Fiedler, loc. cit., 2, p. 1430; Handbook of Pharmaceutical Excipients, loc. cit., page 473).

14) Esterified Compounds of Fatty Acid and Primary Alcohols

These include esterified compounds of fatty acid having 8 to 20 carbon atoms and primary alcohol having 2 to 3 carbon atoms, for example, isopropyl myristate, isopropyl palmitate, ethyl linoleate, ethyl oleate, ethylmyristate etc., with an esterified compound of linoleic acid and ethanol being particularly preferable, also isopropylmyristat and isopropylpalmitat.

15) Glycerol Triacetate or (1,2,3)-Triacetin

This is obtained by esterifying glycerin with acetic anhydride. Glycerol triacetate is commercially available as, e.g. Priacetin® 1580 from Unichema International, or as Eastman™ Triacetin from Eastman, or from Courtaulds Chemicals Ltd. Glycerol triacetate exhibits the following additional characterising data: molecular weight 218.03, $D.^{20,3}$ 1.159-1.163, $n_D^{20}$ 1.430-1.434, water content max. 0.2%, viscosity (250) 17.4 mPa s, acid value max. 0.1, saponification value of about 766-774, triacetin content 97% min. (H. Fiedler, loc. cit., vol 2, page 1580; Handbook of Pharmaceutical Excipients, loc. cit., page 534, manufacturer information).

16) Acetyl Triethyl Citrate

This is obtained by esterification of citric acid and ethanol, followed by acetylation with acetic anhydride, respectively. Acetyl triethyl citrate is commercially available, e.g. under the trade name Citroflex® A-2, from e.g. Morflex Inc.

17) Tributylcitrate or Acetyl Tributyl Citrate

18) Polyglycerol Fatty Acid Esters

These have for example from 2 to 10, e.g. 6 glycerol units. The fatty acid constituent can include both saturated and unsaturated fatty acids having a chain length of from e.g. $C_8$-$C_{18}$. Particularly suitable is e.g. Plurol Oleique CC497 from Gattefossé, having a saponification value of 133-155 and a saponification value of 196-244. Further suitable polyglycerol fatty acid esters include diglyceryl monooleate (DGMO) and Hexaglyn-5-O, as known and commercially available from e.g. Nikko Chemicals Co., Ltd.

19) PEG-Fatty Alcohol Ether

This includes Brij 30™ polyoxyethylene(4) lauryl ether.

20) Fatty Alcohols and Fatty Acids

Fatty acids can be obtained by hydrolysing various animal and vegetable fats or oils, such as olive oil, followed by separation of the liquid acids. The fatty acid/alcohol constituent can include both saturated and mono- or di-unsaturated fatty acids/alcohols having a chain length of from e.g. $C_6$-$C_{20}$. Particularly suitable are, e.g. oleic acid, oleyl alcohol, linoleic acid, capric acid, caprylic acid, caproic acid, tetradecanol, dodecanol, or decanol. Oleyl alcohol is commercially available under the trade mark HD-Eutanol® V from e.g. Henkel KGaA. Oleyl alcohol exhibits the following additional characterising data: acid value max 0.1, hydroxy value of about 210, iodine value of about 95, saponification value max 1, $D.^{20}$ about 0.849, $n_D^{20}$ 1.462, molecular weight 268, viscosity (20°) about 35 mPa s (manufacturer information). Oleic acid exhibits the following additional characterising data: molecular weight 282.47, $D.^{20}$ 0.895, $n_D^{20}$ 1.45823, acid value 195-202, iodine value 85-95, viscosity (250) 26 mPa s (H. Fiedler, loc. cit., volume 2, page 1112; "Handbook of Pharmaceutical Excipients", 2nd Edition, Editors A. Wade and P. J. Weller (1994), Joint publication of American Pharmaceutical Assoc., Washington, USA and The Pharmaceutical Press, London, England, page 325).

21) Tocopherol and its Derivatives (e.g. Acetate)

These include Coviox T-70, Copherol 1250, Copherol F-1300, Covitol 1360 and Covitol 1100.

22) Pharmaceutically Acceptable Oils

Alternatively the lipophilic component comprises e.g. a pharmaceutically acceptable oil, preferably with an unsaturated component such as a vegetable oil.

23) Alkylene Polyol Ethers or Esters

These include $C_{3-5}$alkylene triols, in particular glycerol, ethers or esters. Suitable $C_{3-5}$alkylene trio ethers or esters include mixed ethers or esters, i.e. components including other ether or ester ingredients, for example transesterification products of $C_{3-5}$alkylene trio esters with other mono-, di- or poly-ols. Particularly suitable alkylene polyol ethers or esters are mixed $C_{3-5}$alkylene triol/poly-($C_{2-4}$alkylene)glycol fatty acid esters, especially mixed glycerol/polyethylene- or polypropyleneglycol fatty acid esters.

Especially suitable alkylene polyol ethers or esters include products obtainable by transesterification of glycerides, e.g. triglycerides, with poly-($C_{2-4}$alkylene)glycols, e.g. poly-ethylene glycols and, optionally, glycerol. Such transesterification products are generally obtained by alcoholysis of glycerides, e.g. triglycerides, in the presence of a poly-($C_{2-4}$alkylene) glycol, e.g. polyethylene glycol and, optionally, glycerol (i.e. to effect transesterification from the glyceride to the poly-alkylene glycol/glycerol component, i.e. via poly-alkylene glycolysis/glycerolysis).

In general such reaction is effected by reacting the indicated components (glyceride, polyalkylene glycol and, optionally, glycerol) at elevated temperature under an inert atmosphere with continuous agitation.

Preferred glycerides are fatty acid triglycerides, e.g. ($C_{10-22}$fatty acid) triglycerides, including natural and hydrogenated oils, in particular vegetable oils. Suitable vegetable oils include, for example, olive, almond, peanut, coconut, palm, soybean and wheat germ oils and, in particular, natural or hydrogenated oils rich in ($C_{12-18}$fatty acid) ester residues. Preferred polyalkylene glycol materials are polyethylene glycols, in particular polyethylene glycols having a molecular weight of from ca. 500 to ca. 4,000, e.g. from ca. 1,000 to ca. 2,000.

Suitable alkylene polyol ethers or esters include mixtures of $C_{3-5}$alkylene triol esters, e.g. mono-, di- and tri-esters in variable relative amount, and poly($C_{2-4}$alkylene)glycol mono- and di-esters, together with minor amounts of free $C_{3-5}$alkylene triol and free poly-($C_{2-5}$alkylene)glycol. As hereinabove set forth, the preferred alkylene triol moiety is glyceryl; preferred polyalkylene glycol moieties include polyethylene glycol, in particular having a molecular weight of from ca. 500 to ca. 4,000; and preferred fatty acid moieties will be $C_{10-22}$fatty acid ester residues, in particular saturated $C_{10-22}$fatty acid ester residues.

Particularly suitable alkylene polyol ethers or esters include transesterification products of a natural or hydrogenated vegetable oil and a polyethylene glycol and, optionally, glycerol; or compositions comprising or consisting of glyceryl mono-, di- and tri-$C_{10-22}$fatty acid esters and polyethylene glycol mono- and di-$C_{10-22}$fatty esters (optionally together with, e.g. minor amounts of free glycerol and free polyethylene glycol).

Preferred vegetable oils, polyethylene glycols or polyethylene glycol moieties and fatty acid moieties in relation to the above definitions are as hereinbefore set forth.

Particularly suitable alkylene polyol ethers or esters as described above for use in the present invention include those commercially available under the trade name Gelucire® from e.g. Gattefossé, in particular the products:

a) Gelucire® 33/01, which has an m.p.=ca. 33-37° C. and a saponification value of ca. 230-255;
b) Gelucire® 39/01, m.p.=ca. 37.5-41.5° C., saponification v.=ca. 225-245;
c) Gelucire® 43/01, m.p.=ca. 42-46° C., saponification v.=ca. 220-240;

Products (a) to (c) above all have an acid value of maximum of 3. The compositions of the invention may include mixtures of such ethers or esters.

24) Hydrocarbons
These include e.g. squalene, available from e.g. Nikko Chemicals Co., Ltd.

25) Ethylene Glycol Esters
These include Monthyle® (ethylene glycol monostearate), available from e.g. Gattefossé.

26) Pentaerythriol Fatty Acid Esters and Polyalkylene Glycol Ethers
These include, for example pentaerythrite-dioleate, -distearate, -monolaurate, -polyglycol ether, and -monostearate as well as pentaerythrite-fatty acid esters (Fiedler, loc. cit., 2, p. 1158-1160, incorporated herein by reference).

Some of these, e.g. (1-3, 5-6, 8-9, 12-13, 19), display surfactant-like behaviour and may also be termed co-surfactants.

The lipophilic component preferably comprises 5 to 85% by weight of the composition of the invention, e.g. 10 to 85%; preferably 15 to 60% by weight, more preferably about 15 to about 40% by weight.

Where the carrier medium comprises a hydrophilic component in addition to the lipophilic component and the surfactant the relative proportions of the lipophilic component(s), hydrophilic component(s) and the surfactant(s) lie within the "Microemulsion" region on a standard three way plot graph.

The compositions of the invention include a hydrophilic component or phase.

Suitable hydrophilic compounds include:
1) Polyethylene Glycol Glyceryl $C_8$-$C_{10}$ Fatty Acid Esters
The fatty acid ester may include mono and/or di and/or tri fatty acid esters. It optionally includes both saturated and unsaturated fatty acids having a chain length of from e.g. $C_8$-$C_{10}$. The polyethylene glycols may have e.g. from 5 to 10 [$CH_2$—$CH_2$—O] units, e.g. 7 units. A particularly suitable fatty acid ester is polyethylene glycol (7) glyceryl monococoate, which is commercially available, e.g. under the trade name Cetiol® HE, e.g. from Henkel KGaA. Cetiol® HE has a D. (20°) of 1.05, an acid value of less than 5, a saponification value of about 95, a hydroxyl value of about 180 and an iodine value of less than 5 (H. Fiedler, loc. cit., vol 1, page 337) or Lipestrol E-810.

2) N-Alkylpyrrolidone
Particularly suitable is, e.g. N-Methyl-2-pyrrolidone, e.g. as commercially available under the trade name Pharmasolve™, from e.g. International Specialty Products (ISP). N-methylpyrrolidone exhibits the following additional characterising data: molecular weight 99.1, D.$^{25}$ 1.027-1.028, purity (as area % by GC) (including Methyl Isomers) 99.85% min (H. Fiedler, loc. cit., vol 2, page 1004, manufacturer information).

3) Benzyl Alcohol
This is commercially available from e.g. Merck or may be obtained by distillation of benzyl chloride with potassium or sodium carbonate. Benzyl alcohol exhibits the following additional characterising data: molecular weight 108.14, D. 1.043-1.049, $n_D$ 1.538-1.541. (H. Fiedler, loc. cit., vol 1, page 238; Handbook of Pharmaceutical Excipients, loc. cit., page 35).

4) Triethyl Citrate
It is obtained esterifying citric acid and ethanol. Triethyl citrate is commercially available, e.g. under the trade names Citroflex® 2, or in a pharmaceutical grade under the name TEC-PG/N, from e.g. Morflex Inc. Particularly suitable is triethyl citrate which has molecular weight of 276.3, a specific gravity of 1.135-1.139, a refractive index of 1.439-1.441, a viscosity (250) of 35.2 mPa s, assay (anhydrous basis) 99.0-100.5%, water max. 0.25% (Fiedler, H. P., loc. cit., vol 1, page 371; "Handbook of Pharmaceutical Excipients", loc. cit., page 540).

5) Polyethylene Glycol 400 (PEG400)
Other suitable hydrophilic compounds include transcutol ($C_2H_5$—[O—($CH_2$)$_2$]$_2$—OH), glycofurol (also known as tetrahydrofurfuryl alcohol polyethylene glycol ether), 1,2-propylene glycol, dimethylisosorbide (Arlasolve), polyethylene glycol, triethyleneglycol, ethylacetate, and ethyl lactate.

The hydrophilic component may comprise 5 to 60% by weight of the composition of the invention, e.g. 10 to 50%; preferably 10 to 40% by weight, more preferably about 10 to about 30% by weight.

The hydrophilic component may comprise a mixture of two or more hydrophilic components. The ratio of main hydrophilic component to hydrophilic co-component is typically from about 0.5:1 to about 2:1.

The compositions of the present invention preferably contain one or more surfactants to reduce the interfacial tension thereby providing thermodynamic stability.

Surfactants may be complex mixtures containing side products or unreacted starting products involved in the preparation thereof, e.g. surfactants made by polyoxyethylation may contain another side product, e.g. polyethylene glycol.

The or each surfactant preferably has a hydrophilic-lipophilic balance (HLB) value of 8 to 17, especially 10 to 17. The HLB value is preferably the mean HLB value.

Suitable surfactants include:
1) Reaction Products of a Natural or Hydrogenated Castor Oil and Ethylene Oxide
The natural or hydrogenated castor oil may be reacted with ethylene oxide in a molar ratio of from about 1:35 to about 1:60, with optional removal of the polyethyleneglycol component from the products. Various such surfactants are commercially available. Particularly suitable surfactants include polyethyleneglycol-hydrogenated castor oils available under the trade name Cremophor®; Cremophor® RH 40, which has a saponification value of about 50 to 60, an acid value less than about 1, a water content (Fischer) less than about 2%, an $n_D^{60}$ of about 1.453-1.457 and an HLB of about 14-16; and Cremophor® RH 60, which has a saponification value of about 40-50, an acid value less than about 1, an iodine value of less than about 1, a water content (Fischer) of about 4.5-5.5%, an $n_D^{60}$ of about 1.453-1.457 and an HLB of about 15 to 17.

An especially preferred product of this class is Cremophor® RH40. Other useful products of this class are available under the trade names Nikkol® (e.g. Nikkol® HCO-40 and HCO-60), Mapeg® (e.g. Mapeg® CO-40h), Incrocas® (e.g. Incrocas® 40), Tagat® (for example polyoxyethylene-glycerol-fatty acid esters e.g. Tagat® RH 40) and Simulsol OL-50 (PEG-40 castor oil, which has a saponification value of about 55 to 65, an acid value of max. 2, an iodine value of 25 to 35, a water content of max. 8%, and an HLB of about 13, available from Seppic). These surfactants are further described in Fiedler loc. cit.

Other suitable surfactants of this class include polyethyleneglycol castor oils such as that available under the trade name Cremophor® EL, which has a molecular weight (by steam osmometry) of about 1630, a saponification value of about 65 to 70, an acid value of about 2, an iodine value of about 28 to 32 and an $n_D^{25}$ of about 1.471.

2) Polyoxyethylene-Sorbitan-Fatty Acid Esters

These include mono- and tri-lauryl, palmityl, stearyl and oleyl esters of the type known and commercially available under the trade name Tween® (Fiedler, loc. cit. p. 1615 ff) from Uniqema including the products:

Tween® 20 [polyoxyethylene(20)sorbitanmonolaurate],
Tween® 21 [polyoxyethylene(4)sorbitanmonolaurate],
Tween® 40 [polyoxyethylene(20)sorbitanmonopalmitate],
Tween® 60 [polyoxyethylene(20)sorbitanmonostearate],
Tween® 65 [polyoxyethylene(20)sorbitantristearate],
Tween® 80 [polyoxyethylene(20)sorbitanmonooleate],
Tween® 81 [polyoxyethylene(5)sorbitanmonooleate], and
Tween® 85 [polyoxyethylene(20)sorbitantrioleate].

Especially preferred products of this class are Tween® 20 and Tween® 80.

3) Polyoxyethylene Fatty Acid Esters

These include polyoxyethylene stearic acid esters of the type known and commercially available under the trade name Myrj® from Uniqema (Fiedler, loc. cit., 2, p. 1042). An especially preferred product of this class is Myrj® 52 having a $D^{25}$ of about 1.1, a melting point of about 40 to 44° C., an HLB value of about 16.9., an acid value of about 0 to 1 and a saponification no. of about 25 to 35.

4) Polyoxyethylene-Polyoxypropylene Co-Polymers and Block Co-Polymers or Poloxamers These include the type known and commercially available under the trade names Pluronic® and Emkalyx® (Fiedler, loc. cit., 2, p. 1203). An especially preferred product of this class is Pluronic® F68 (poloxamer 188) from BASF, having a melting point of about 52° C. and a molecular weight of about 6800 to 8975. A further preferred product of this class is Synperonic® PE L44 (poloxamer 124) from Uniqema.

5) Polyoxyethylene Mono Esters of a Saturated $C_{10}$ to $C_{22}$

These include $C_{18}$ substituted e.g. hydroxy fatty acid; e.g. 12 hydroxy stearic acid PEG ester, e.g. of PEG about e.g. 600-900 e.g. 660 Daltons MW, e.g. Solutol® HS 15 from BASF, Ludwigshafen, Germany. According to the BASF technical leaflet MEF 151E (1986) comprises about 70% polyethoxylated 12-hydroxystearate by weight and about 30% by weight unesterified polyethylene glycol component. Solutol HS 15 has a hydrogenation value of 90 to 110, a saponification value of 53 to 63, an acid number of maximum 1, and a maximum water content of 0.5% by weight.

6) Polyoxyethylene Alkyl Ethers

These include polyoxyethylene glycol ethers of $C_{12}$ to $C_{18}$ alcohols, e.g. Polyoxyl 2-, 10- or 20-cetyl ether or Polyoxyl 23-lauryl ether, or polyoxyl 20-oleyl ether, or Polyoxyl 2-, 10-, 20- or 100-stearyl ether, as known and commercially available e.g. under the trade mark Brij® from Uniqema. An especially preferred product of this class is e.g. Brij® 35 (Polyoxyl 23 lauryl ether) or Brij® 98 (Polyoxyl 20 oleyl ether) (Fiedler, loc. cit., 1, pp. 259; Handbook of Pharmaceutical Excipients, loc. cit., page 367). Similarly suitable products include polyoxyethylene-polyoxypropylene-alkyl ethers, e.g. polyoxyethylene-polyoxypropylene-ethers of $C_{12}$ to $C_{18}$ alcohols, e.g. polyoxyethylen-20-polyoxypropy-lene-4-cetylether which is known and commercially available under the trade mark Nikkol PBC® 34, from e.g. Nikko Chemicals Co., Ltd. (Fiedler, loc. cit., vol. 2, pp. 1239). Polyoxypropylene fatty acid ethers, e.g. Acconon® E are also suitable.

7) Sodium Alkyl Sulfates and Sulfonates, and Sodium Alkyl Aryl Sulfonates

These include sodium lauryl sulfate, which is also known as sodium dodecyl sulfate and commercially available, e.g. under the trade name Texapon K12® from Henkel KGaA.

8) Water Soluble Tocopheryl Polyethylene Glycol Succinic Acid Esters (TPGS)

These include those with a polymerisation number ca 1000, e.g. available from Eastman Fine Chemicals Kingsport, Tex., USA.

9) Polyglycerol Fatty Acid Esters

These include those with e.g. from 10 to 20, e.g. 10 glycerol units. The fatty acid constituent may include both saturated and unsaturated fatty acids having a chain length of from e.g. $C_8$-$C_{18}$. Particularly suitable is e.g. decaglycerylmonolaurat or decaglycerylmonomyristat, as known and commercially available under the trade mark Decaglyn® 1-L or Decaglyn® 1-M or Decaglyn 1-0, respectively, from e.g. Nikko Chemicals C., Ltd (Fiedler, loc. cit., vol. 2, pp. 1228).

10) Alkylene Polyol Ethers or Esters

These include $C_{3-5}$alkylene triols, in particular glycerol, ethers or esters. Suitable $C_{3-5}$alkylene triol ethers or esters include mixed ethers or esters, i.e. components including other ether or ester ingredients, for example transesterification products of $C_{3-5}$alkylene triol esters with other mono-, di- or poly-ols. Particularly suitable alkylene polyol ethers or esters are mixed $C_{3-5}$alkylene triol/poly-($C_{2-4}$alkylene)glycol fatty acid esters, especially mixed glycerol/polyethylene- or polypropyleneglycol fatty acid esters.

Especially suitable alkylene polyol ethers or esters include products obtainable by transesterification of glycerides, e.g. triglycerides, with poly-($C_{2-4}$alkylene)glycols, e.g. poly-ethylene glycols and, optionally, glycerol.

Such transesterification products are generally obtained by alcoholysis of glycerides, e.g. triglycerides, in the presence of a poly-($C_{2-4}$alkylene)glycol, e.g. polyethylene glycol and, optionally, glycerol (i.e. to effect transesterification from the glyceride to the poly-alkylene glycol/ glycerol component, i.e. via poly-alkylene glycolysis/ gly-cerolysis). In general such reaction is effected by reacting the indicated components (glyceride, polyalkylene glycol and, optionally, glycerol) at elevated temperature under an inert atmosphere with continuous agitation.

Preferred glycerides are fatty acid triglycerides, e.g. ($C_{10-22}$ fatty acid) triglycerides, including natural and hydrogenated oils, in particular vegetable oils. Suitable vegetable oils include, for example, olive, almond, peanut, coconut, palm, soybean and wheat germ oils and, in particular, natural or hydrogenated oils rich in ($C_{12-18}$ fatty acid) ester residues.

Preferred polyalkylene glycol materials are polyethylene glycols, in particular polyethylene glycols having a molecular weight of from ca. 500 to ca. 4,000, e.g. from ca. 1,000 to ca. 2,000.

Suitable alkylene polyol ethers or esters include mixtures of $C_{3-5}$ alkylene triol esters, e.g. mono-, di- and tri-esters in variable relative amount, and poly($C_{2-4}$ alkylene)glycol mono- and di-esters, together with minor amounts of free $C_{3-5}$ alkylene triol and free poly-($C_{2-5}$ alkylene)glycol. As hereinabove set forth, the preferred alkylene triol moiety is glyceryl; preferred polyalkylene glycol moieties include polyethylene glycol, in particular having a molecular weight of from ca. 500 to ca. 4,000; and preferred fatty acid moieties will be $C_{10-22}$ fatty acid ester residues, in particular saturated $C_{10-22}$ fatty acid ester residues.

Particularly suitable alkylene polyol ethers or esters include transesterification products of a natural or hydrogenated vegetable oil and a polyethylene glycol and, optionally, glycerol; or compositions comprising or consisting of glyceryl mono-, di- and tri-$C_{10-22}$ fatty acid esters and polyethylene glycol mono- and di-$C_{10-22}$ fatty esters (optionally together with, e.g. minor amounts of free glycerol and free polyethylene glycol).

Preferred vegetable oils, polyethylene glycols or polyethylene glycol moieties and fatty acid moieties in relation to the above definitions are as hereinbefore set forth.

Particularly suitable alkylene polyol ethers or esters as described above for use in the present invention include those commercially available under the trade name Gelucire® from e.g. Gattefossé, in particular the products:

a) Gelucire® 44/14, m.p.=ca. 42.5-47.5° C., saponification v.=ca. 79-93;
b) Gelucire® 50/13, m.p.=ca. 46-51° C., saponification v.=ca. 67-81;

Products (a) to (b) above all have an acid value of maximum of 2.

Alkylene polyol ethers or esters having an iodine value of maximum 2 are generally preferred. The compositions of the invention may include mixtures of such ethers or esters.

Gelucire® products are inert semi-solid waxy materials with amphiphilic character. They are identified by their melting point and their HLB value. Most Gelucire® grades are saturated polyglycolised glycerides obtainable by polyglycolysis of natural hydrogenated vegetable oils with polyethylene glycols. They are composed of a mixture of mono-, di- and tri-glycerides and mono- and di-fatty acid esters of polyethylene glycol. Particularly suitable is Gelucire® 44/14 which has a nominal melting point of 44° C. and an HLB of 14. It is obtained by reacting hydrogenated palm kernels and/or hydrogenated palm oils with polyethylene glycol 1500. It consists of approximately 20% mono-, di- and triglycerides, 72% mono- and di-fatty acid esters of polyethylene glycol 1500 and 8% of free polyethylene glycol 1500. The fatty acid distribution for Gelucire® 44/14 is as follows: 4-10 $C_8$, 3-9 $C_{10}$, 40-50 $C_{12}$, 14-24 $C_{14}$, 4-14 $C_{16}$, 5-15 $C_{18}$. Gelucire® 44/14 exhibits the following additional characterising data: acid value of max. 2, iodine value of max. 2, saponification value of 79-93, hydroxyl value of 36-56, peroxide value of max. 6, alkaline impurities max. 80, water content max. 0.50, free glycerol content max. 3, monoglycerides content 3.0-8.0. (H. Fiedler, loc. cit., vol 1, page 676; manufacturer information).

11) Polyethylene Glycol Glyceryl Fatty Acid Esters

The fatty acid ester may include mono and/or di and/or tri fatty acid ester. The fatty acid constituent may include both saturated and unsaturated fatty acids having a chain length of from e.g. $C_{12}$-$C_{18}$. The polyethylene glycols may have e.g. from 10 to 40 [$CH_2$—$CH_2$—O] units, e.g. 15 or 30 units. Particularly suitable is polyethylene glycol (15) glyceryl monostearat which is commercially available, e.g. under the trade name TGMS®-15, e.g. from Nikko Chemicals Co., Ltd. Other suitable glyceryl fatty acid esters include polyethylene glycol (30) glyceryl monooleate which is commercially available, e.g. under the trade name Tagat® 0, e.g. from Goldschmidt (H. Fiedler, loc. cit., vol. 2, p. 1502-1503), and Tagat O2 (polyethylene glycol (20) glycerol monooleate, as well as Tagat L (polyethylene glycol (30) glycerol monolaurate) and Tagat L2 (polyethylene glycol (20) glycerol monolaurate), all e.g. from Goldschmidt (H. Fiedler, loc. cit., vol. 2, p. 1502-1503). A further suitable polyethylene glycol glyceryl fatty acid ester is Tagat TO.

12) Sterols and Derivatives Thereof

These include cholesterols and derivatives thereof, in particular phytosterols, e.g. products comprising sitosterol, campesterol or stigmasterol, and ethylene oxide adducts thereof, for example soya sterols and derivatives thereof, e.g. polyethylene glycol sterols, e.g. polyethylene glycol phytosterols or polyethylene glycol soya sterols. The polyethylene glycols may have e.g. from 10 to 40 [$CH_2$—$CH_2$—O] units, e.g. 25 or 30 units. Particularly suitable is polyethylene glycol (30) phytosterol which is commercially available, e.g. under the trade name Nikkol BPS®-30, e.g. from Nikko Chemicals Co., Ltd. Further suitable is polyethylene glycol (25) soya sterol which is commercially available, e.g. under the trade name Generol® 122 E 25, e.g. from Henkel (H. Fiedler, loc. cit., vol. 1, p. 680).

13) Transesterified, Polyoxyethylated Caprylic-Capric Acid Glycerides

These include those that are commercially available under the trade name Labrasol® from e.g. Gattefossé. Labrasol® has an acid value of max. 1, a saponification value of 90-110, and an iodine value of max. 1 (H. Fiedler, loc. cit., vol 2, page 880).

14) Sugar Fatty Acid Esters

These include those of $C_{12}$-$C_{18}$ fatty acids, e.g. sucrose monolaurate, e.g. Ryoto L-1695®, which is commercially available from e.g. Mitsubishi-Kasei Food Corp., Tokyo, Japan.

15) PEG Sterol Ethers

These include those having, e.g. from 5 to 35 [$CH_2$—$CH_2$—O] units, e.g. 20 to 30 units., e.g. Solulan® C24, which is commercially available from e.g. Amerchol.

16) Dioctylsodiumsulfosuccinate

This is commercially available under the trade mark Aerosol OT® from e.g. American Cyanamid Co. (Fiedler, loc. cit., 1, p. 118), or di-[2-ethylhexyl]-succinate (Fiedler, loc. cit., volume 1, p. 487).

17) Phospholipids
    These include in particular lecithins (Fiedler, loc. cit., volume 2, p. 910, 1184). Suitable lecithins include, in particular, soya bean lecithins.
18) Salts of Fatty Acids, Fatty Acid Sulfates and Sulfonates
    These include those of e.g. $C_6$-$C_{18}$, fatty acids, -fatty acid sulfates and sulfonates, as known and commercially available from e.g. Fluka.
19) Salts of Acylated Amino Acids
    These include those of $C_6$-$C_{18}$, acylated amino acids, e.g. sodium lauroyl sarcosinate, which is commercially available from e.g. Fluka.
20) Medium or Long-Chain Alkyl, e.g. $C_6$-$C_{18}$, Ammonium Salts
    These include $C_6$-$C_{18}$ acylated amino acids e.g. cetyl trimethyl ammonium bromide, which is commercially available from e.g. E. Merck AG.

The surfactant may comprise 5 to 90% by weight of the composition of the invention; preferably 10 to 85% by weight, more preferably 15 to 60% by weight.

The compositions of the present invention may contain co-solvents to reduce the interfacial tension thereby providing thermodynamic stability. Suitable co-solvents include lower alkanols such as ethanol. While the use of ethanol in the compositions is not essential, it has been found to be of particular advantage to increase the solubility of camptothecin derivative. This is because storage characteristics are improved, in particular the risk of active agent precipitation following encapsulation procedures is reduced. Thus the shelf life stability may be extended by employing ethanol or some other such co-component as an additional ingredient of the composition. The ethanol may comprise 0 to 60% by weight of the composition; preferably 5 to about 30% by weight and more preferably about 5 to 20% by weight.

Certain embodiments of the compositions of the invention include additives for example antioxidants, antimicrobial agents, enzyme inhibitors, stabilizers, preservatives, flavours, sweeteners and other components such as those described in Fiedler, H. P., loc. cit.

Preferred antioxidants include ascorbyl palmitate, butyl hydroxy anisole (BHA), butyl hydroxy toluene (BHT) and citric acid. The antioxidant ascorbyl palmitate is especially preferred.

These additives or ingredients may comprise about 0.05 to 5% by weight of the total weight of the composition. Antioxidants, antimicrobial agents, enzyme inhibitors, stabilizers or preservatives typically provide up to about 0.05 to 1% by weight based on the total weight of the composition. Sweetening or flavouring agents typically provide up to about 2.5 or 5% by weight based on the total weight of the composition.

In another aspect, the invention provides a process for preparing a spontaneously dispersible pharmaceutical composition containing a camptothecin derivative as an active agent, which process comprises bringing the active agent and a carrier medium comprising (1) a lipophilic component, (2) a surfactant, (3) a hydrophilic component, and optionally (4) a co-solvent into intimate admixture.

The carrier medium can be prepared separately before bringing the active agent into intimate admixture with the carrier medium. Alternatively the two or more of the components of the carrier medium can be mixed together with the active agent.

The spontaneously dispersible pharmaceutical composition is preferably a microemulsion preconcentrate as herein defined.

The spontaneously dispersible pharmaceutical composition preferably spontaneously or substantially spontaneously forms an o/w (oil-in-water) emulsion, e.g. microemulsion, when diluted with an aqueous medium such as water to a dilution of 1:1 to 1:300, e.g. 1:1 to 1:70, especially 1:10 to 1:70, more especially e.g. 1:10, or in the gastric juices of a patient after oral application.

In another aspect, the invention provides a process for the preparing a microemulsion containing a camptothecin derivative as an active agent, which process comprises:
(i) bringing the active agent and a carrier comprising (1) a lipophilic component, (2) a surfactant, (3) a hydrophilic component, and optionally (4) a co-solvent into intimate admixture to form a spontaneously dispersible pharmaceutical composition; and
(ii) diluting the spontaneously dispersible pharmaceutical composition in an aqueous medium to form the microemulsion.

As mentioned above, the active agent may be present in an amount by weight of up to about 20% by weight of the composition of the invention, e.g. from about 0.05% by weight. The active agent is preferably present in an amount of about 0.5 to about 15% by weight of the composition, more preferably in an amount of about 1.0 to about 5% by weight of the composition.

The lipophilic component preferably comprises about 5 to about 85% by weight of the composition of the invention, e.g. about 10 to about 85%; preferably about 15 to about 60% by weight.

The hydrophilic component may comprise about 5 to about 60% by weight of the composition of the invention, e.g. about 5 to about 50%; preferably about 5 to about 40% by weight, more preferably about 5 to about 30% by weight. It may comprise a mixture of two or more hydrophilic components.

The surfactant may comprise about 5 to about 90% by weight of the composition of the invention; preferably about 15 to about 85% by weight, more preferably about 20 to about 60% by weight.

The co-solvent may comprise about 0 to about 90% by weight of the composition of the invention, preferably about 0 to about 30% by weight, more preferably about 0 to about 20% by weight, e.g. about 15 or 20% by weight.

The relative proportion of the active agent(s), the lipophilic component(s), the surfactant(s) the hydrophilic component(s), and the co-solvents (when present) preferably lie within the "Microemulsion" region on a standard three way plot graph. The compositions will therefore be of high stability that are capable, on addition to an aqueous medium, of providing microemulsions, for example having a mean particle size of <200 nm.

When the composition of the invention is a microemulsion preconcentrate it may be combined with water or an aqueous solvent medium to obtain an emulsion, for example a microemulsion. The emulsion or microemulsion may be administered enterally, for example orally, for example in the form of a drinkable solution.

When the composition of the invention is a microemulsion preconcentrate a unit dosage of the microemulsion preconcentrate is preferably used to fill orally administrable capsule shells. The capsule shells may be soft or hard capsule shells, for example made of gelatine. Each unit dosage will suitably contain from 0.1 to 100 mg active agent, for example 0.1 mg, 0.25 mg, 0.5 mg, 1 mg, 2 mg, 10 mg, 15 mg, 25 mg or 50 mg, preferably between 0.1 and 1 mg of the active agent. Such unit dosage forms are suitable for administration 1 to 5 times daily depending upon the particular purpose of therapy, the phase of therapy and the like. However, if desired, the compositions may be in drink solution form and may include water or any other aqueous system, e.g. fruit juice, milk, and the like, to provide e.g. colloidal systems, suitable for drinking, e.g. with a dilution of from about 1:10 to about 1:100.

The compositions of the invention, e.g. those in the examples hereinafter, may show good stability characteristics as indicated by standard stability trials, for example having a shelf life stability of up to one, two or three years, and even longer. One group of compositions of the invention may be of high stability that are capable, on addition to water, of providing aqueous microemulsions having an average particle size of <200 nm (2,000 Å), e.g. <150 nm (1,500 Å), e.g. <100 nm (1,000 Å).

The compositions of the invention exhibit especially advantageous properties when administered orally; for example in terms of consistency and high level of bioavailability obtained in standard bioavailability trials.

Pharmacokinetic parameters, for example drug substance absorption and measured for example as blood levels, also become surprisingly more predictable and problems in administration with erratic absorption may be eliminated or reduced. Additionally the pharmaceutical compositions are effective with biosurfactants or tenside materials, for example bile salts, being present in the gastrointestinal tract. That is, the pharmaceutical compositions of the present invention are fully dispersible in aqueous systems comprising such natural tensides and thus capable of providing emulsion or microemulsion systems and/or particulate systems in situ which are stable. The function of the pharmaceutical compositions upon oral administration remain substantially independent of and/or unimpaired by the relative presence or absence of bile salts at any particular time or for any given individual. The compositions of this invention may also reduce variability in inter- and intra-patient dose response.

The utility of the compositions of the invention may be observed in standard clinical tests in, for example, known indications of active agent at dosages giving therapeutically effective active agent blood levels. Any increased bioavailability of the compositions of the invention may be observed in standard animal tests and in clinical trials.

The dose of the active agent in the compositions of the invention is of the same order as, or up to half, that used in known compositions containing the active agent. The compositions of the invention show activity at concentrations from about 0.1 mg to about 40 mg/day of active agent, preferably from about 0.1 mg to about 20 mg/day, e.g. most preferably from about 0.1 to about 1 mg/day of active agent.

A typical dose for the active agent is from 0.1 to 1 mg/day for treating proliferative diseases or diseases that are associated with or triggered by persistent angiogenesis. A proliferative disease is mainly a tumor disease (or cancer) (and/or any metastases). The inventive compositions are particularly useful for treating a tumor which is a breast cancer, lung cancer, gastrointestinal cancer, including esophageal, gastric, small bowel, large bowel and rectal cancer, glioma, sarcoma such as those involving bone, cartilage, soft tissue, muscle, blood and lymph vessels, ovarian cancer, myeloma, female cervical cancer, endometrial cancer, head and neck cancer, mesothelioma, renal cancer, ureter, bladder and urethral cancers, prostate cancer, skin cancers and melanoma. In particular, the inventive compositions are particularly useful for treating (i) a breast tumor; a lung tumor, e.g., non-small cell lung tumor; a gastrointestinal tumor, e.g., a colorectal tumor; or a genitourinary tumor, e.g., a prostate tumor; or (ii) a proliferative disease that is refractory to the treatment with other chemotherapeutics; or (iii) a tumor that is refractory to treatment with other chemotherapeutics due to multidrug resistance. In a broader sense of the invention, a proliferative disease may furthermore be a hyperproliferative condition, such as a leukemia, lymphoma, multiple myeloma.

Thus in another aspect, the present invention provides a method of treatment of a subject suffering from a disorder treatable with a camptothecin derivative comprising administering a therapeutically effective amount of a pharmaceutical composition of the invention to a subject in need of such treatment.

The invention is illustrated by the following Examples.

EXAMPLES

In the following examples the pharmaceutically active agent is Compound A, described above as 7-t-butoxyiminomethylcamptothecin. The microemulsions of the present invention can be administered as a drink solution or can be encapsulated in soft (gelatine or non-gelatin) and hard (gelatine and non-gelatin) capsules.

Example 1

Filled Capsule or Oral Solution

The formulation contains:

| | |
|---|---|
| Compound A | 1 mg |
| Cremophor RH 40 | 447 mg |
| Corn oil glycerides | 358 mg |
| Propylene glycol 1,2 | 90 mg |
| Ethanol | 99 mg |
| Ascorbyl palmitate | 5 mg |

Example 2

Filled Capsule or Oral Solution

The formulation contains:

| | |
|---|---|
| Compound A | 1 mg |
| Vitamin E TPGS | 340 mg |
| Propylen Glycol Monocaprylate | 161 mg |
| PEG400 | 343 mg |
| Ethanol | 150 mg |
| Ascorbyl palmitate | 5 mg |

Example 3

Filled Capsule or Oral Solution

The formulation contains:

| | |
|---|---|
| Compound A | 1 mg |
| Vitamin E TPGS | 358 mg |
| Triethylcitrate | 268 mg |
| PEG400 | 268 mg |
| Ethanol | 100 mg |
| Ascorbyl palmitate | 5 mg |

Example 4

Filled Capsule or Oral Solution

The formulation contains:

| | |
|---|---|
| Compound A | 1.5 mg |
| Vitamin E TPGS | 360 mg |
| Triethylcitrate | 270 mg |
| Dimethylisosorbit | 270 mg |
| Ethanol | 100 mg |

Example 5

Filled Capsule or Oral Solution

| | |
|---|---|
| Compound A | 1 mg/g |
| Vitamin E TPGS | 447 mg/g |
| Capmul MCM C8 | 179 mg/g |
| PEG400 | 268 mg/g |
| Ethanol | 99 mg/g |
| Ascorbylpalmitate | 5 mg/g |

Example 6

Filled Capsule or Oral Solution

| | |
|---|---|
| Compound A | 1 mg/g |
| Cremophor RH40 | 180 mg/g |
| Triethylcitrate | 360 mg/g |
| Ethylacetate | 360 mg/g |
| Ethanol | 100 mg/g |

The compositions of all six examples are prepared whereby the carrier components are mixed and the active ingredient is dissolved therein whilst stirring. The mixtures of the formulations described in the above Examples may be filled into hard gelatine capsules and sealed using the Quali-Seal™ sealing technique.

The invention claimed is:

1. A spontaneously dispersible pharmaceutical composition comprising about 0.05 to about 20% by weight of 7-t-butoxyiminomethylcamptothecin and
   a carrier medium comprising
      about 5 to about 85% by weight of a lipophilic component selected from the group consisting of $C_8$-$C_{10}$ fatty acid monoglycerides and diglycerides, a refined glycerol-transesterified corn oil, triethylcitrate, and castor oil;
      about 5 to about 90% by weight of a surfactant component selected from the group consisting of polyethylene-hydrogenated castor oil and Vitamin E TPGS;
      about 5 to about 60% by weight of a hydrophilic component selected from the group consisting of propylene glycol, PEG400 and ethylacetate; and
      about 5 to 20% of ethanol by weight as a co-solvent,
   all weights based on the total composition, wherein the spontaneously dispersible pharmaceutical composition is a microemulsion preconcentrate.

2. A spontaneously dispersible pharmaceutical composition as claimed in claim 1, further comprising one or more additive selected from the group of antioxidants consisting of ascorbyl palmitate, butyl hydroxy anisole, butyl hydroxy toluene and citric acid.

3. A spontaneously dispersible pharmaceutical composition as claimed in claim 2, wherein the antioxidant is ascorbyl palmitate.

4. A spontaneously dispersible pharmaceutical according to claim 1 that is suitable for oral administration.

5. A spontaneously dispersible pharmaceutical composition as claimed in claim 4, further comprising ascorbyl palmitate as an antioxidant.

6. A composition as claimed in claim 4 wherein the surfactant comprises polyethyleneglycol-hydrogenated castor oil and Vitamin E TPGS.

7. A spontaneously dispersible pharmaceutical composition according to claim 1 in a unit dosage form.

8. A spontaneously dispersible pharmaceutical composition as claimed in claim 7 in soft or hard gelatin encapsulated form.

9. A spontaneously dispersible pharmaceutical composition as claimed in claim 7 in oral solution form.

10. A process for preparing a spontaneously dispersible pharmaceutical composition, wherein the spontaneous dispersible pharmaceutical composition is a microemulsion preconcentrate, containing about 0.05 to about 20% by weight of 7-t-butoxyiminomethylcamptothecin as an active agent, which process comprises bringing the active agent and a carrier medium comprising
   (1) about 5 to about 85% by weight of a lipophilic component,
   (2) about 5 to about 90% by weight of a surfactant,
   (3) about 5 to about 60% by weight of a hydrophilic component, and
   (4) about 5 to 20% by weight of ethanol as co-solvent into intimate admixture, all weights based on the total composition.

11. A process for preparing a spontaneously dispersible pharmaceutical composition as claimed in claim 10 wherein the carrier medium further comprises one or more additives selected from the group of antioxidants consisting of ascorbyl palmitate, butyl hydroxy anisole, butyl hydroxy toluene and citric acid.

12. A process for the preparing a spontaneously dispersible pharmaceutical composition as claimed in claim 11 wherein the antioxidant is ascorbyl palmitate.

* * * * *

UNITED STATES PATENT AND TRADEMARK OFFICE
CERTIFICATE OF CORRECTION

PATENT NO. : 8,518,961 B2  Page 1 of 1
APPLICATION NO. : 11/718275
DATED : August 27, 2013
INVENTOR(S) : Isabel Ottinger It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1386 days.

Signed and Sealed this

Fifteenth Day of September, 2015

Michelle K. Lee
*Director of the United States Patent and Trademark Office*